(12) United States Patent
Dohmen et al.

(10) Patent No.: US 10,231,785 B2
(45) Date of Patent: Mar. 19, 2019

(54) DETERMINATION OF AN IMPLANT ORIENTATION RELATIVE TO A BONE

(71) Applicant: Brainlab AG, Munich (DE)

(72) Inventors: Lars Dohmen, Munich (DE); Mario Schubert, Poing (DE); Anna Wiedenmann, Feldkirchen (DE)

(73) Assignee: Brainlab AG, Munich (DE)

( * ) Notice: Subject to any disclaimer, the term of this patent is extended or adjusted under 35 U.S.C. 154(b) by 47 days.

(21) Appl. No.: 15/516,534

(22) PCT Filed: May 8, 2015

(86) PCT No.: PCT/EP2015/060202
§ 371 (c)(1),
(2) Date: Apr. 3, 2017

(87) PCT Pub. No.: WO2016/180439
PCT Pub. Date: Nov. 17, 2016

(65) Prior Publication Data
US 2018/0235703 A1    Aug. 23, 2018

(51) Int. Cl.
*A61B 5/00* (2006.01)
*A61B 34/10* (2016.01)
(Continued)

(52) U.S. Cl.
CPC ............ *A61B 34/10* (2016.02); *A61B 5/1118* (2013.01); *A61B 5/1122* (2013.01); *A61B 34/20* (2016.02);
(Continued)

(58) Field of Classification Search
CPC ..... A61B 5/1121; A61B 5/1122; A61B 34/10; A61B 2034/102; A61B 2034/104; A61B 2034/108; A61F 2/4657; A61F 2/4668
See application file for complete search history.

(56) References Cited

U.S. PATENT DOCUMENTS

| 5,995,738 A | 11/1999 | DiGioia, III et al. |
| 8,983,813 B2 | 3/2015 | Miles et al. |
| (Continued) | | |

FOREIGN PATENT DOCUMENTS

| DE | 20 2010 008 404 U1 | 12/2010 |
| WO | 2012097873 A1 | 7/2012 |
| WO | 2013117909 A1 | 8/2013 |

OTHER PUBLICATIONS

European Patent Office, International Search Report and Written Opinion for PCT/2015/060202 dated Oct. 30, 2015, pp. 1-14, NL.
(Continued)

*Primary Examiner* — Max Hindenburg
(74) *Attorney, Agent, or Firm* — Tucker Ellis LLP (57) ABSTRACT

Implant orientation data representing a range of functional orientations of a first implant part relative to a first bone is determined. The first implant part is part of an implant pair to be implanted in an associated patient. The implant pair includes the first implant part and a second implant part. Second implant orientation data representing an orientation of the second implant part relative to a second bone is acquired. Implant shape data representing shapes of the first and the second implant parts is acquired. Activity data representing a desired activity of the associated patient is acquired. The desired activity has an associated original range of motion between the first bone and the second bone. The implant orientation data is determined based on the second implant orientation data, the implant shape data, and the activity data.

20 Claims, 6 Drawing Sheets

(51) Int. Cl.
*A61B 34/20* (2016.01)
*A61B 5/11* (2006.01)
*A61F 2/32* (2006.01)
*A61F 2/46* (2006.01)

(52) U.S. Cl.
CPC .......... *A61F 2/4684* (2013.01); *A61B 5/4571* (2013.01); *A61B 5/4595* (2013.01); *A61B 2034/102* (2016.02); *A61B 2034/104* (2016.02); *A61B 2034/105* (2016.02); *A61B 2034/2051* (2016.02); *A61F 2/32* (2013.01); *A61F 2002/4633* (2013.01)

(56) References Cited

U.S. PATENT DOCUMENTS

| | | |
|---|---|---|
| 9,295,172 B2 * | 3/2016 | Nagayasu ............ H02G 3/0487 |
| 9,889,021 B2 * | 2/2018 | Park ........................ A61B 5/055 |
| 2001/0008981 A1 | 7/2001 | Masini |
| 2003/0184577 A1 | 10/2003 | Petrella et al. |
| 2006/0095047 A1 | 5/2006 | de la Barrera |
| 2008/0294265 A1 | 11/2008 | Warkentine et al. |
| 2010/0076563 A1 | 3/2010 | Otto et al. |

OTHER PUBLICATIONS

Widmer et al., Compliant positioning of total hip components for optimal range of motion, Journal of Orthopaedic Research 22 (2004) pp. 815-821, University of Basel, Switzerland.

* cited by examiner

DETERMINATION OF AN IMPLANT ORIENTATION RELATIVE TO A BONE

RELATED APPLICATIONS

This application is a national phase application of International Application No. PCT/EP2015/060202, filed May 8, 2015, the disclosure of which is incorporated herein by reference in its entirety.

BACKGROUND

The present invention relates to a data processing method, performed by a computer, for determining implant orientation data representing a range of functional orientations of a first implant part relative to a first bone and to a corresponding computer program and system.

SUMMARY

Implanting an artificial joint in a patient is a widely used medical task. The artificial joint is formed by an implant pair comprising a first implant part to be attached to a first bone which interacts with a second implant part to be attached to a second bone. The effect of the artificial joint strongly depends on whether or not the implant parts are suitably positioned on, in particular aligned or oriented with, the respective bones. A suitable functionality of the artificial joint, which is also referred to as implant joint, can typically not only be achieved for a single orientation between an implant part and a bone, but over a range of orientations. While the location of an implant part relative to the bone might have an influence on the functionality of the artificial joint, the present invention concentrates on the orientation of an implant part relative to a bone. In particular, the present invention relates to determining implant orientation data representing a range of functional orientations of a first implant part relative to the first bone. It shall be noted that the expression "functional orientations" means those orientations which would result in a desired functionality of the artificial joint.

In this document, an implant part is a part of an artificial joint which is assigned to a bone. This means that an implant part might comprise one or more components which make up the implant part.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

According to the present invention, a data processing method performed by a computer for determining implant orientation data representing a range of functional orientations of a first implant part relative to a first bone, wherein the first implant part is a part of an implant pair which further comprises a second implant part for a second bone and the implant pair is envisaged to be implanted in a patient, comprises the step of acquiring second implant orientation data representing the orientation of the second implant part relative to the second bone. This means that the orientation of the second implant part relative to the second bone is given, such that only the range of orientations of the first implant part relative to the first bone is to be determined. The second implant orientation data is for example measured, assumed, calculated or received from a planning process.

The method further comprises the steps of acquiring implant shape data representing the shapes of the first and second implant parts and of acquiring activity data representing at least one desired activity of the patient to be possible after implanting the implant. The shape of the implant parts limits the interaction of the two implant parts, and in particular limits the possible joint orientations of the artificial joint. A desired activity is an activity the patient shall be able to perform with the artificial joint. An activity is for example an activity out of a predefined set of so-called activities of daily living (ADL), which can be considered as an atlas of activities.

Still further, the method comprises the step of calculating the implant orientation data from the second implant orientation data, the implant shape data and the activity data. Since the second implant orientation data and the implant shape data are given, the activity data essentially defines the joint orientations of the artificial joint which shall be attainable once the implant pair is implanted in the patient. Calculating the implant orientation data does therefore for example mean to calculate a range of orientations which comprises those orientations of the first implant part relative to the first bone such that the joint orientations of the artificial joint defined by the activity data are attainable.

For the sake of brevity, this document also uses the expressions "orientation" or "orientation of the first/second implant part" as a short form of "orientation of the first/second implant part relative to the first/second bone".

The implant does for example form a ball-and-socket joint, which is also referred to as ball joint. Typical ball-and-socket joints are the hip joint between the femur and the acetabulum of the pelvis or the shoulder joint formed between the humerus and the glenoid cavity of the shoulder blade. The implant pair is therefore suitable for replacing the hip joint or the shoulder joint.

The shapes of the first and second implant parts depend on the several factors, such as the type of joint to be replaced, the particulars (like gender or size) of the patient and the model of the implant parts. The implant shape data is for example acquired from a database in which the shapes of a plurality of first and second implant parts are stored.

In one embodiment, each desired activity has an associated range of motion between the first bone and the second bone. A range of motion does for example define orientations between the first bone and the second bone which are required in order to perform the corresponding activity. A range of motion may be defined by the maximum movement, that is deflection, between the two bones during the activity, or by a plurality of orientations between the first bone and the second bone during the activity.

An orientation between two bones or two implant parts is typically defined by three rotations in three distinct, preferably orthogonal, rotational dimensions defined by corresponding axes of rotation. It is thus a point in a three-dimensional orientation space which is spanned by the axes of rotation. In the medical field, the axes of rotation are typically axes which are anatomically meaningful. The axes are for example the axes of flexion-extension rotation, adduction-abduction rotation and internal-external rotation.

In this case, a range of motion associated with an activity is for example defined by a required range of the flexion-extension rotation, a required range of the adduction-abduction rotation and a required range of the internal-external rotation. An orientation of the first implant relative to the first bone then is a functional orientation if it allows the artificial joint to assume joint orientations which enables those three ranges of rotational movement.

An orientation of an implant part relative to a bone typically also is a point in a three-dimensional orientation space which is spanned by three axes of rotation. However, those axes of rotation are for example defined with respect to the bone. A range of orientations is then a part of the three-dimensional orientation space, and thus a volume. However, the orientation space can also be two-dimensional or one-dimensional, depending on the type of implant.

In one embodiment, the implant orientation data represents the orientation of the first implant part relative to the first bone in two rotational dimensions. This is particularly advantageous if the implant pair forms a ball-and-socket joint, in which the first implant part exhibits a rotational symmetry. It is then only necessary to consider the orientation in two rotational dimensions. Those two rotational dimensions for example correspond to the inclination and the anteversion of the first implant part.

In this embodiment, the range of functional orientations is a two-dimensional area which is defined in a co-ordinate system which is spanned by the two axes of the inclination and the anteversion.

In one embodiment, the range of functional orientations is displayed on a display unit. This allows a user to identify the range of functional orientations.

In one embodiment, the limitation to the range of functional orientations caused by a particular desired activity is displayed alone or together with the range of functional orientations. This allows a user to identify the influence of a particular desired activity, in particular if the limitations imposed by a plurality of desired activities are displayed. In other words, the boundaries to the range of functional orientations corresponding to the respective desired activities are identified.

In one embodiment, calculating the implant orientation data involves determining, for a trial orientation, whether or not the ranges of motion of all desired activities can be achieved with an implant joint formed by the implant pair for the trial orientation and adding the trial orientation to the implant orientation data if this is the case. In this embodiment, a trial orientation of the first implant part relative to the first bone is assumed and tested. If the trial orientation allows all desired activities, it is considered as a functional orientation.

This embodiment for example involves to test a plurality of trial orientations, and therefore a grid of discrete trial orientations. Due to the nature of an artificial joint formed by an implant pair, there is typically a set of adjacent orientations which are functional orientations. In one implementation, a functional orientation which has at least one neighboring trial orientation which is not a functional orientation is assumed as a functional orientation which forms the boundary of the range of functional orientations. In this manner, a closed range of functional orientations is obtained, and all orientations within this range, even if they were not trial orientations, are assumed to be functional orientations.

In one embodiment, each desired activity is associated with a set of one or more relative orientations between the first and the second bone, similar to the situation as described above, and a range of motion of a desired activity can be achieved if the implant joint allows all relative orientations in the set of relative orientations. If there is only one relative orientation in the set, this relative orientation typically is the most extreme relative orientation between the bones. If there are two or more relative orientations, they typically resemble the trajectory of the two bones during the corresponding activity.

In one embodiment, calculating the implant orientation data involves calculating a zero joint orientation of the implant joint from the second implant orientation data and the trial orientation. The zero joint orientation is the orientation between the first and second implant parts of the implant joint in which the first and second bones are in a neutral position relative to each other. The zero joint orientation is calculated for the trial orientation of the first implant part, because it depends on how the first implant part is oriented relative to the first bone.

The neutral position between the first and second bones is a known position in the field of medicine and depends on the type of joint. In the hip joint as an example, the neutral position is the position in which the mechanical axis of the femur lies in a sagittal plane, for instance parallel to the midsagittal plane, and the mechanical axis and posterior condylar line of the femur describe a plane which is parallel to the frontal plane of the pelvis. The posterior condylar line connects the most posterior and distal femoral points. It might, however, not be possible to acquire or sample those points, for example during surgery. In this case, an option is to acquire the ankle epicondyle piriformis (AEP) plane defined by a piriformis point (the proximal point of the femur shaft axis), the center of the epicondyle axis and an ankle point of the flexed leg. A direction orthogonal to this AEP plane corresponds to the direction of the posterior condylar axis and thus forms, together with the mechanical axis, a plane which is parallel to the frontal plane of the pelvis in the neutral position.

The neutral position between two bones typically is the origin relative to which a range of motion is defined. This neutral position is achieved for a particular joint orientation of the implant joint which depends on how the implant parts are oriented relative to their respective bones, which in the present embodiment is defined by the trial orientation regarding the first implant part and the second implant orientation data regarding the second implant part.

Since, in this embodiment, the neutral position is the origin or reference for the ranges of motion, this means that the zero joint orientation is the origin of the implant joint relative to which a corresponding joint orientation of the implant joint must be attainable in order to allow a particular range of motion between the two bones. Therefore, in one implementation, determining whether or not a range of motion of a desired activity can be achieved by the implant joint involves determining whether or not the implant joint can reach the range of motion from the zero joint orientation. If the range of motion associated with an activity is defined by the flexion-extension rotation, the adduction-abduction rotation and the internal-external rotation, the attainable joint orientations of the implant joint can be defined with respect to the same axes with the zero joint orientation as the origin.

Determining whether or not the implant joint can reach the range of motion therefore means that it is tested whether or not the implant joint allows a deflection from the zero joint orientation which comprises the range of motion associated with a desired activity.

If a range of motion of a desired activity is defined by a set of one or more relative orientations between the first bone and the second bone, which are typically given relative to the neutral position between the two bones, it is tested whether or not the implant joint can reach a corresponding relative orientation between the first implant part and the second implant part relative to the zero joint orientation. In one implementation, it is determined whether or not the first and second implant parts impinge for a particular relative orientation. Whether or not the implant parts impinge is for example determined by a collision detection of 3D models of the first implant part and the second implant part. The 3D models for example are the implant shape data or are derived from the implant shape data. In one implementation, a particular relative position between the two 3D models is assumed, wherein the relative location between the 3D models is predetermined and the orientation between the two 3D models corresponds to a relative orientation between the first bone and the second bone for a particular desired activity. It is then determined whether or not the two 3D models intersect each other. If they intersect each other, the two implant parts impinge, and if they do not intersect each other, the implant parts do not impinge.

It shall be noted that more sophisticated approaches for collision detection can be applied, for example approaches which allow a particular translational shift between the two 3D models depending on the joint orientation and/or which incorporate additional information such as ligaments of the joint or bone structures. The range of motion of an artificial is in some cases not only limited by the shape of the implant parts, but is further limited by bones, in particular the bones the implant parts are attached to. In those cases, an implant part and a bone or two bones collide before the implant parts collide. This can be considered in the collision detection by also modeling the bones, for example as a part of a 3D model.

In one implementation, whether or not the implant parts impinge is determined by an analytical analysis of the implant shape data instead of by a collision detection using 3D models.

In one embodiment, at least one desired activity has an associated reduced range of motion between the first bone and the second bone and calculating the implant orientation data involves calculating extended implant orientation data for the reduced range of motion.

As explained above, a particular activity requires a particular range of motion, which represents required relative orientations between the first bone and the second bone and is also referred to as original range of motion. The set of desired activities results in a particular range of functional orientations. It might, however, occur that it is impossible to obtain an orientation of the first implant part relative to the first bone which is within the range of functional orientations, for example due to the structure of the first bone which does not allow such an orientation of the first implant part. In this embodiment, a reduced range of motion, which for example represents a smaller maximum deflection from the neutral position as the original range of motion, is considered and new implant orientation data is calculated for the reduced range of motion.

Since the reduced range of motion typically results in a larger range of functional orientations than the original range of motion, the new implant orientation data can be referred to as extended implant orientation data. So if a particular orientation of the first implant part relative to the first bone lies in the extended orientation data, but not in the implant orientation data, this means that this orientation only allows a reduced range of motion, such that the corresponding desired activity might be limited, though not completely precluded. If for example a particular activity is defined as requiring a 120 degrees flexion, a reduced range of motion may be defined as being for example 118 degrees or 115 degrees of flexion. So if a particular orientation of the first implant part relative to the first bone only allows 118 degrees of flexion, but not 120 degrees, the corresponding desired activity cannot be fully performed, but possibly good enough.

In one embodiment, the method further involves the steps of tracking the actual orientation of the first implant part relative to the first bone and of determining whether or not the tracked orientation is within the range of functional orientations represented by the extended implant orientation data. Tracking the actual orientation of the first implant part is preferably performed using a medical tracking or navigation system which is able to determine the relative position between two objects, such as the first implant part and the first bone. Tracking can be performed as an accompanying step during an actual surgery in which the first implant part is to be attached to the first bone or as an accompanying task during a mock surgery which is performed on a dummy patient for training purposes. However, the expression "tracking" in this embodiment also encompasses determining a planned orientation of the first implant part relative to the first bone during a planning procedure.

The present embodiment allows to determine whether or not the tracked orientation is within an extended part of the range of functional orientations represented by the extended implant orientation data.

In one embodiment, a desired activity has associated a plurality of reduced ranges of motion in which the range of motion is reduced step-wise. This results in step-wise incremented extended implant orientation data. This represents different grades of non-fulfillment of the requirements of a particular desired activity.

In one implementation, the method further comprises the step of tracking the actual orientation of the first implant part relative to the first bone. The details of tracking are the same as in the preceding embodiment.

In one implementation, the embodiment further comprises the step of determining whether or not the tracked orientation is within the range of functional orientations represented by the implant orientation data. In this implementation, it can for example be determined if the actual orientation is a functional orientation and the first implant part can be attached to the first bone with the actual orientation. The information whether or not the tracked orientation is within the range of functional orientations is preferably output to a user, for example as an acoustic signal and/or a visual signal indicated, for example, by a lamp or on a display device.

In one embodiment, the method further comprises the step of outputting guidance information which indicates how the orientation of the first implant part relative to the first bone has to be changed, compared to the actual orientation as it is tracked, in order to lie within the range of functional orientations. This allows guiding a user who handles the first implant part to a functional orientation of the first implant part.

In one implementation, if the activity data represents a plurality of desired activities, activity implant orientation data is calculated for each of the desired activities and the implant orientation data is the intersection of the activity implant orientation data for all desired activities. This means that, in the first additional step of this embodiment, each desired activity is treated separately and an activity range of functional orientations is calculated for each desired activity. In order to obtain the range of functional orientations for the combination of all desired activities, all separate activity ranges of functional orientations for all the desired activities are intersected in order to find a range of functional orientations which is common to all desired activities.

The present invention further relates to a program which, when running on a computer, causes the computer to perform the method steps of the method described above and/or a program storage medium on which the program is stored, in particular in a non-transitory form.

The present invention further relates to a medical planning system for determining implant orientation data representing a range of functional orientations of a first implant part relative to a first bone, the first implant part being part of an implant pair which further comprises a second implant part for a second bone and to be implanted in a patient, comprising a computer on which the program described above is stored and/or run.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. An embodiment of the data processing method is a use of the computer for performing the data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. An embodiment is directed to the use of such a substance or composition in the data processing method. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web.

Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. For this reason alone, no surgical or therapeutic activity and in particular no surgical or therapeutic step is necessitated or implied by carrying out the invention.

This invention can be part of a next generation of image-based or image-free hip software. The most advantage of this invention is the definition of a patient-specific safe-zone for a functional valid pelvis implant position based on desired activities respectively desired range-of-motion values.

BRIEF DESCRIPTION OF THE DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
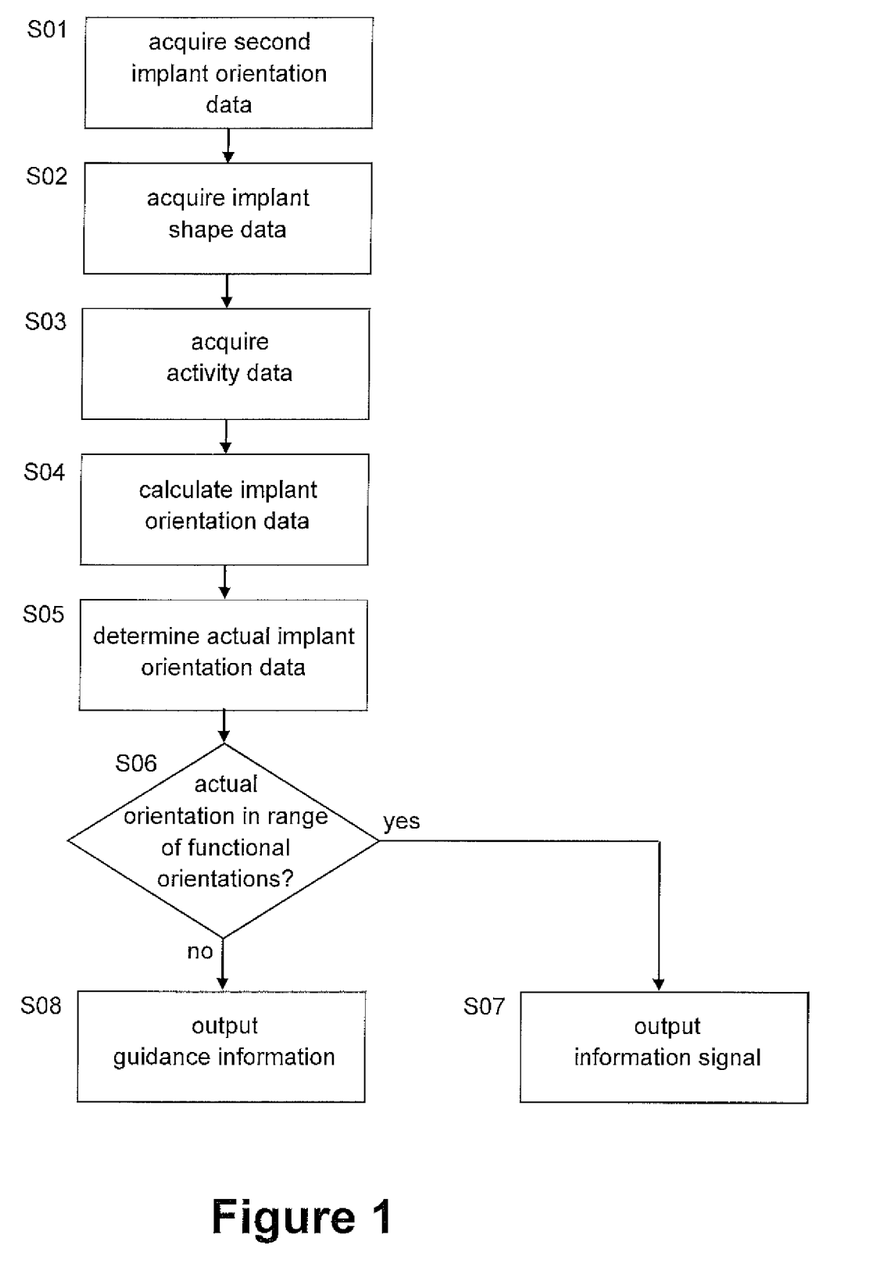
FIG. 1 a flowchart of a method for determining implant orientation data.

FIG. 1 shows a flow diagram of a method for determining implant orientation data representing a range of functional orientations of a first implant part relative to a first bone. The first implant part and a second implant part together form an implant pair which forms an implant joint, which is also referred to as artificial joint. In an exemplary embodiment, the first bone is a pelvis and the second bone is a femur. In this case, an orientation of the first implant part relative to the pelvis is defined by an anteversion angle and an inclination angle. Those two angles span a two-dimensional orientation space.

An aspect of the present invention is to obtain a set of one or more desired activities of a patient who will receive the artificial joint and to determine a suitable orientation of the first implant part such that all desired activities are possible. Such an orientation is referred to as functional orientation. There is typically not a single functional orientation, such that there is a range of functional orientations in the two-dimensional orientation space. It shall be noted that the expression "orientation of an implant part" actually means "orientation of an implant part relative to a bone".

The present invention aims at determining the implant orientation data for the first implant part, assuming that the orientation of the second implant part relative to the second bone is already set. Step S01 therefore involves acquiring second implant orientation data representing the orientation of the second implant part relative to the second bone.

Step S02 involves acquiring implant shape data representing the shapes of the first implant part and the second implant part. The method according to the present invention is performed for a particular implant pair, the parts of which exhibit a particular shape, which includes the size of the implant parts. The implant shape data represents the three-dimensional geometry of the two implant parts. The shapes of the implant parts limit the interaction between the implant parts, and therefore the range of motion of the implant joint.

Step S03 involves acquiring activity data representing at least one desired activity of the patient to be possible after implanting the implant. The desired activities are for example selected from an atlas of activities of daily living (ADL), which is a predetermined list of activities such as basic activities like different hygiene activities, dressing, self-feeding or mobility, and instrumental activities such as housework, shopping or using objects. For example, one or more desired activities are selected from the atlas of activities of daily living.

Each desired activity has an associated range of motion between the first bone and the second bone. Such a range of motion describes the relative orientations between the first and second bone which are required in order to perform the corresponding activity. A range of motion or a relative orientation is typically defined with respect to a neutral position between the first and second bone.

Step S04 involves calculating the implant orientation data from the second implant orientation data, the implant shape data and the activity data. As explained above, the implant orientation data describes a range of functional orientations of the first implant part relative to the first bone which allow all desired activities, depending on the particular implant pair and the given orientation of the second implant part relative to the second bone. With step S04, the task of determining the implant orientation data is fulfilled. The subsequent steps are optional.

Step S05 involves determining the actual orientation of the first implant part relative to the first bone. Step S06 involves deciding whether or not the actual orientation of the first implant part lies in the range of functional orientations as represented by the implant orientation data. If the actual orientation lies within the range of functional orientations (yes in step S06), the method proceeds to step S07, in which an information signal is output. If it does not (no in step S06), the method proceeds to step S08 in which guidance information is output. The guidance information indicates how the orientation of the first implant part with respect to the first bone has to be changed such that the actual orientation of the first implant part lies within the range of functional orientations. Outputting the guidance information, and therefore step S08, is optional.

Figure 2:
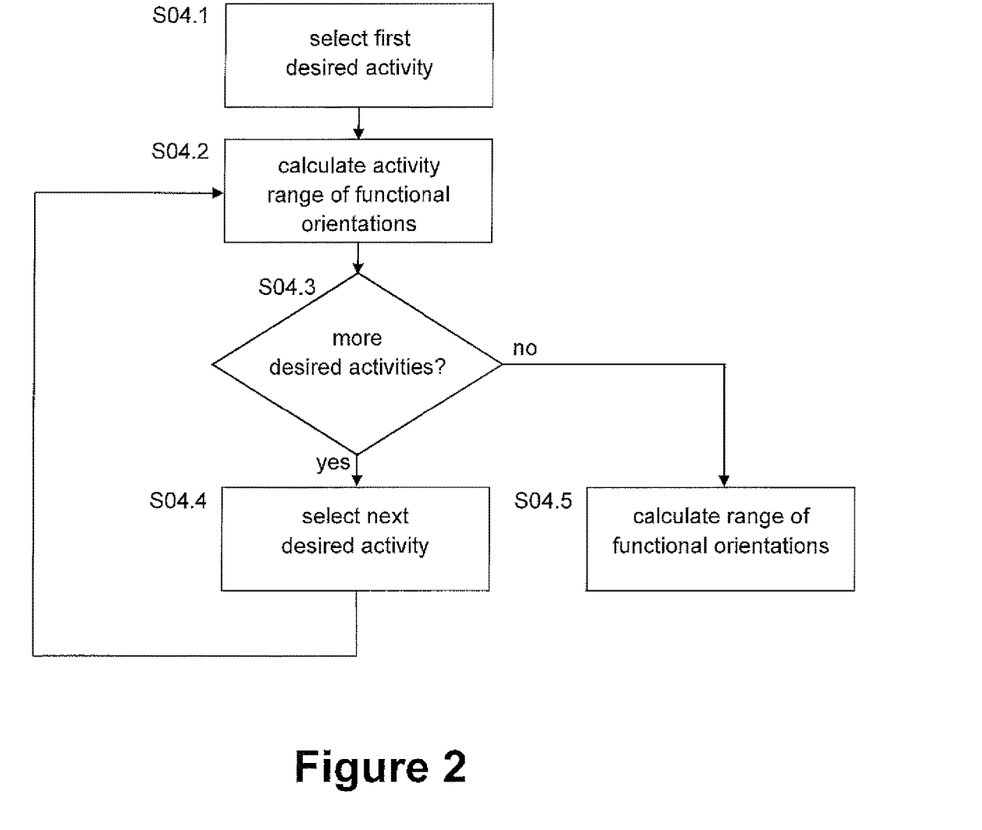
FIG. 2 details of the calculation step of FIG. 1.

FIG. 2 shows details of step S04 of FIG. 1.

Step S04.1 involves selecting a first desired activity represented by the activity data. Step S04.2 involves calculating an activity range of functional orientations of the first implant part relative to the first bone. This is a range of functional orientations of the first implant which allows the selected desired activity.

Step S04.3 involves determining if there are more desired activities represented by the activity data. If this is the case (yes instep S04.3), step S04.4 involves selecting the next desired activity represented by the activity data and the method returns to step S04.2, which is performed with the new selected desired activity.

If there are no more desired activities (no in step S04.3), the method proceeds to step S04.5. This step involves calculating an intersection of all activity ranges of functional orientations and outputs the intersection as the implant orientation data.

In other words, steps S04.2, S04.3 and S04.4 iterate through all desired activities represented by the activity data and calculate a respective activity range of functional orientations for each desired activity.

Figure 3:
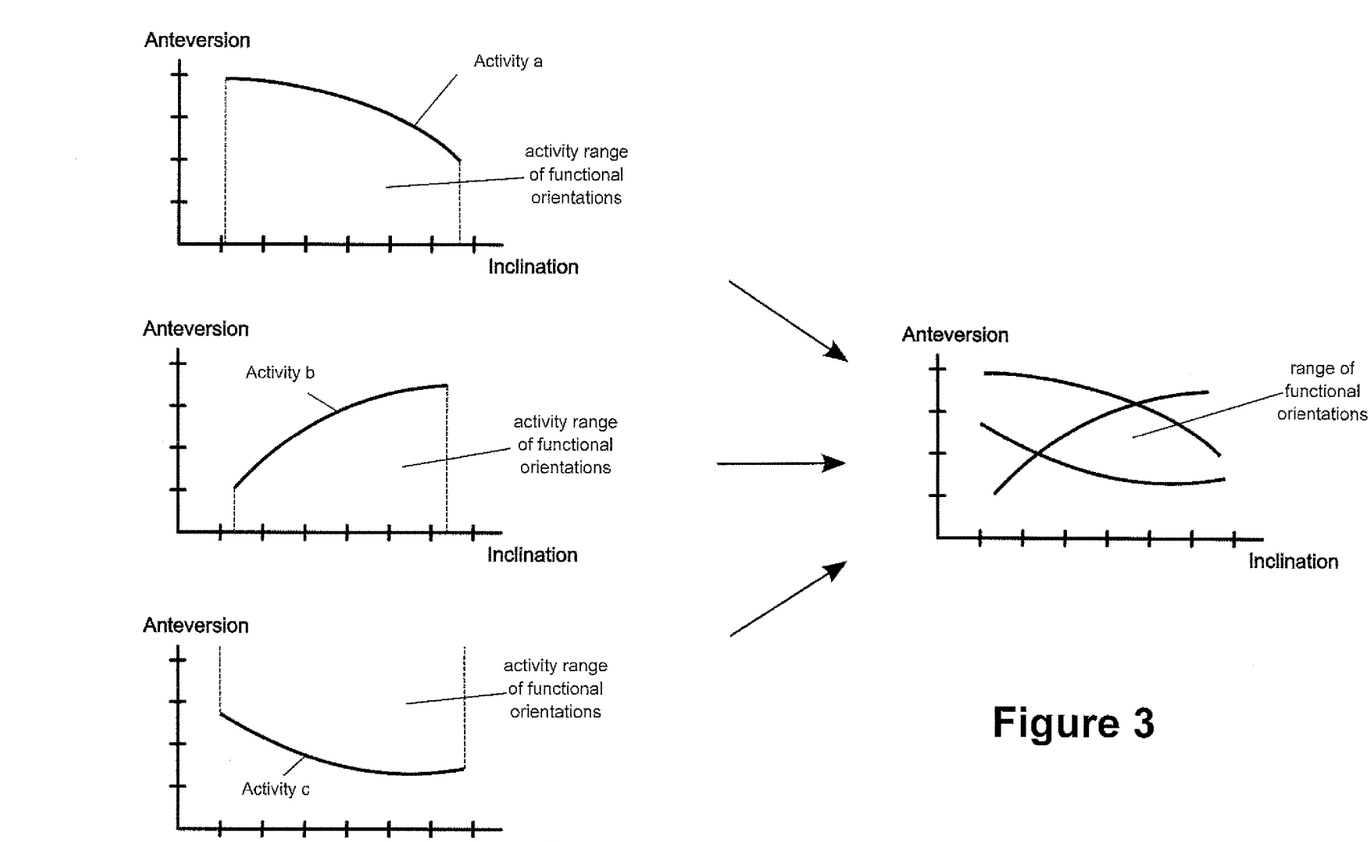
FIG. 3 boundaries of functional orientations for a plurality of activities.

The left part of FIG. 3 shows three graphs depicting three activity ranges of functional orientations for three activities a, b, and c limited by respective boundaries. The activity ranges are shown in an orientation plane defined by the inclination angle and the anteversion angle of the first implant part relative to the first bone. The right part of FIG. 3 shows the intersection of the three activity ranges of functional orientations, which results in the range of functional orientations of the first implant part which allows all three activities a, b, and c. It is understood that any other number of desired activities can be selected.

Figure 4:
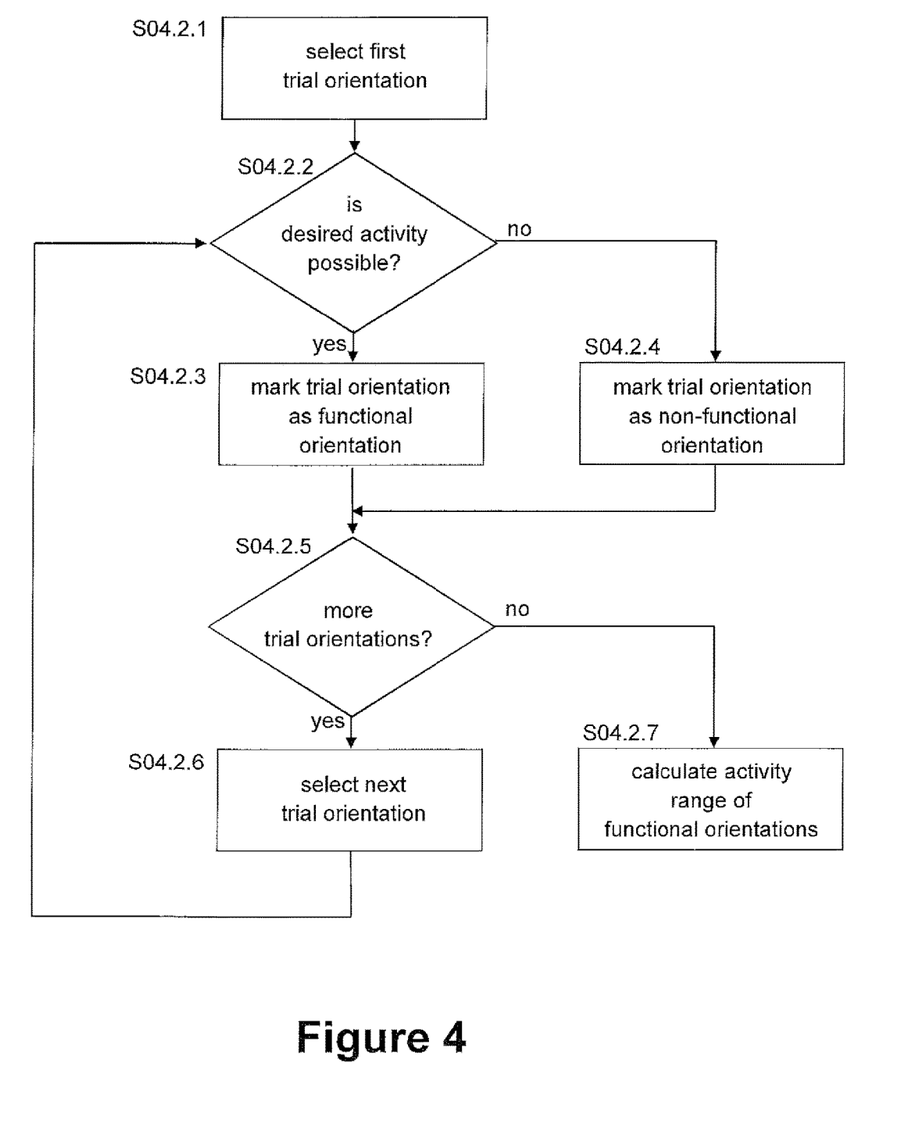
FIG. 4 details of the step of calculating a boundary of FIG. 2.

FIG. 4 shows details of the step S04.2 of FIG. 2, which is the step of calculating an activity range of functional orientations.

In the present embodiment, an activity range of functional orientations is calculated by testing a plurality of trial orientations for whether or not they allow the selected desired activity. In other words, the orientation space, which in the present embodiment is an orientation plane, is sampled by a plurality of trial orientations. Due to the nature of an artificial joint, it can be assumed that an activity range of functional orientations is limited by a closed activity boundary and all orientations within the closed boundary are functional orientations.

Step S04.2.1 involves selecting a first trial orientation.

Step S04.2.2 involves determining whether or not the selected trial orientation allows the selected desired activity. If this is the case (yes in step S04.2.2), the selected trial orientation is marked as a functional orientation in step S04.2.3. If this is not the case (no in step S04.2.2), the selected trial orientation is marked as a non-functional orientation in step S04.2.4.

The method then proceeds to step S04.2.5 in which it is determined whether or not there are more trial orientations to test. If this is the case (yes in step S04.2.5), the next trial orientation is selected in step S04.2.6 and the method returns to step S04.2.2. If this is not the case (no in step S04.2.5), the method proceeds to step S04.2.7.

In step S04.2.7, the activity range of functional orientations is calculated based on the classification of the trial orientations into functional and non-functional orientations. In one implementation, step S04.2.7 involves to determine all trial orientations which are functional orientations and which have at least one neighbouring trial orientation which is a non-functional orientation. Those trial orientations then form the boundary of the activity range of functional orientations.

As outlined above, whether or not a desired activity is possible as determined in step S04.2.2 depends on the second implant orientation data, the implant shape data and the activity data as well as the selected trial orientation. In the following explanation, it is assumed that a range of motion associated with a desired activity corresponds to a set of one or more relative orientations between the first bone and the second bone.

This set of relative orientations between the bones is transformed into a set of one or more relative orientations between the first implant part and the second implant part. This transformation depends on the second implant orientation data and the selected trial orientation. It is then determined whether or not the implant pair can reach all relative orientations in the set of relative orientations between the implant parts. This can be done by a collision detection approach which uses 3D models of the implant parts. If, for a particular relative orientation, the 3D models of the first and second implant part do not collide or intersect with each other, then the implant parts can reach said orientation. If the implant parts can reach all relative orientations in the set of relative orientations between the implant parts, the selected trial orientation allows the corresponding desired activity.

Instead of implementing a collision detection based on 3D models, an analytical approach can be implemented.

Determining whether or not the implant pair can reach all relative orientations in the set of relative orientations between the implant parts might consider additional information, such as ligaments of the joint or the shape of a bone.

Instead of transforming the relative orientations associated with a desired activity into relative orientations between the implant parts, it is possible to transform the range of possible relative orientations of the two implant parts into a range of possible relative orientations between the two bones. This transformation can be calculated based on the second implant orientation data and the selected trial orientation. The transformed range of possible relative orientations can then be compared to the set of one or more relative orientations between the first bone and the second bone which is associated with the desired activity.

Figure 5:
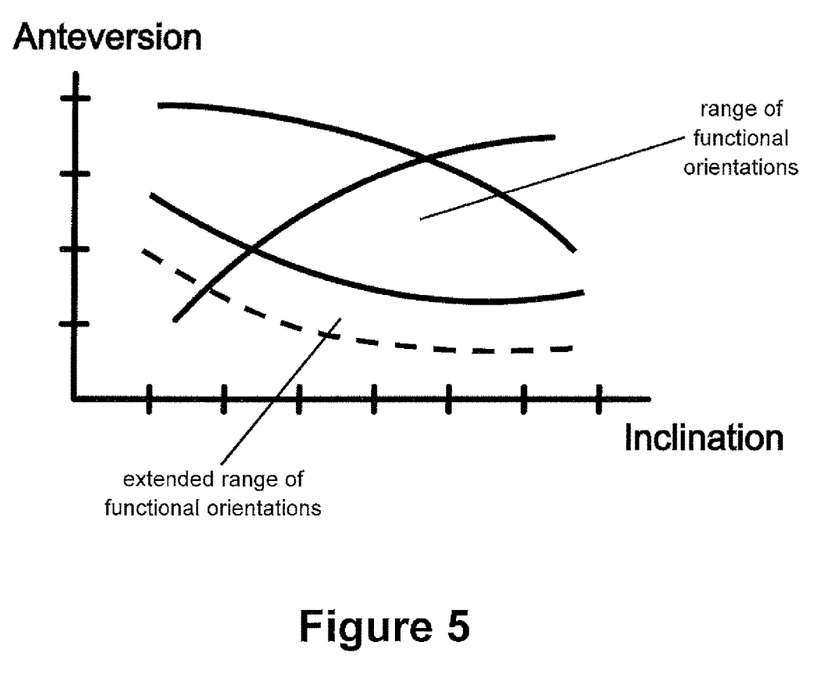
FIG. 5 a range of functional orientations for a reduced range of motion.

In an optional extension of the present embodiment, a desired activity does not only have an associated range of motion between the first bone and the second bone, but also at least one associated reduced range of motion between the first bone and the second bone. The reduced range of motion is smaller than the (original) range of motion and does for example allow the corresponding desired activity to be performed in a restricted manner. Since the range of motion is reduced, the resulting activity range of functional orientations is extended, as shown in FIG. 5 for the activity c. This results in an extended range of functional orientations, which is represented by extended implant orientation data. In FIG. 5, the extended activity range of functional orientations for activity c is shown by the dashed line.

It is understood that one or more reduced ranges of motion can be associated with one desired activity, a plurality of desired activities or all desired activities.

A reduced range of motion for a desired activity is also represented by the activity data and therefore acquired in step S03. Step S04 does then not only involve calculating the implant orientation data, but also the extended implant orientation data. Step S06 can then comprise to determine whether or not the actual orientation of the first implant part is within an extended range of functional orientations, but not in the original range of functional orientations. The result of this determination can also be output in step S07.

Figure 6:
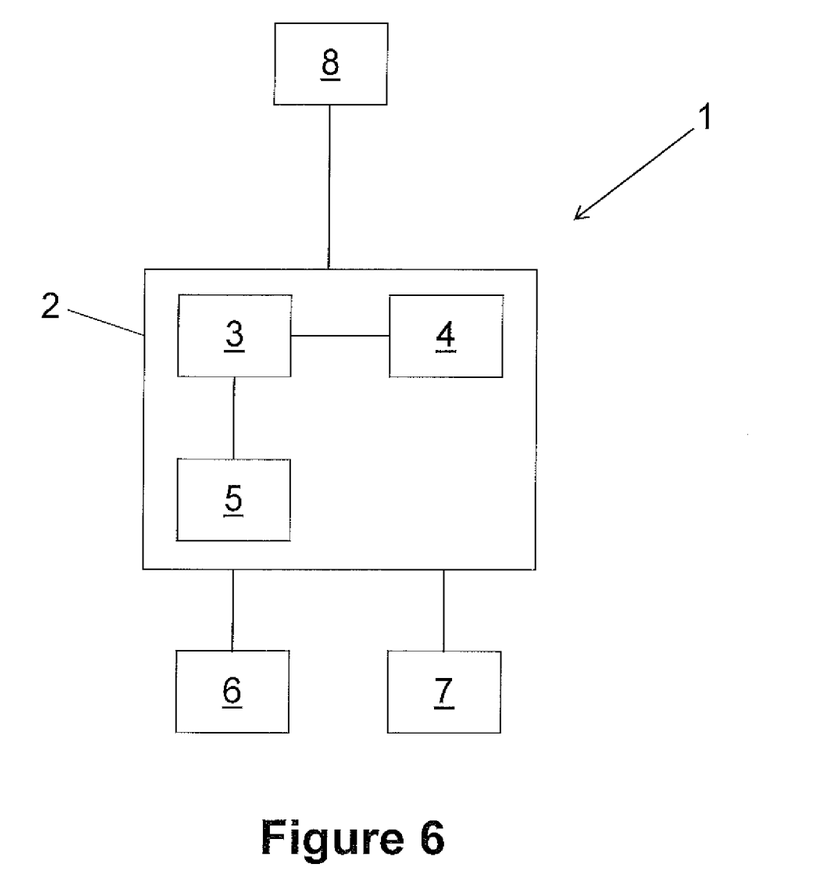
FIG. 6 a system for performing the method.

FIG. 6 shows a system 1 for determining implant orientation data as explained above. The system 1 comprises a computer 2 including a central processing unit 3, a memory unit 4 and an interface 5. The computer 2 is connected to an input unit 6, such as a mouse, a keyboard or a touch-sensitive surface, and an output unit 7 such as a display, a speaker or a tactile sensation generating unit. The input unit 6 is for example used to identify the particular implant pair for which the method is to be performed. The computer is further connected to an actual orientation determining unit 8. The computer 2 is connected to the units 6, 7 and 8 via the interface 5. The memory unit 4 stores working data, such as the implant orientation data, the implant shape data and the activity data, and a program code which instructs the central processing unit 3 to perform the method as explained above.

The actual orientation determining unit 8 can be a tracking unit which tracks a marker device attached to the first implant part or to an instrument to which the first implant part is attached.

The tracking unit can for example be a stereoscopic camera or a transmitter or a receiver for electromagnetic radiation in an EM tracking system. However, the actual orientation determining unit might be a planning unit which plans the orientation between the first implant part and the first bone. The planning unit might be a software module which is executed on the computer 2.

It is claimed:

1. A data processing method for determining implant orientation data representing a range of functional orientations of a first implant part relative to a first bone, the first implant part being part of an implant pair to be implanted in an associated patient, the implant pair comprising the first implant part and a second implant part, the method comprising:

acquiring, by a computer, second implant orientation data representing an orientation of the second implant part relative to a second bone;

acquiring, by the computer, implant shape data representing shapes of the first and the second implant parts;

acquiring, by the computer, activity data representing a desired activity of the associated patient, the desired activity having an associated original range of motion between the first bone and the second bone;

determining, by the computer, the implant orientation data based on the second implant orientation data, the implant shape data, and the activity data, the determining the implant orientation data comprising:

determining a zero joint orientation, in which the first and the second bone are in a neutral position relative to each other, of the implant joint based on a trial orientation and the second implant orientation data;

determining, for the trial orientation, that the associated original range of motion of the desired activity can be achieved from the zero joint orientation with an implant joint formed by the implant pair for the trial orientation; and adding the trial orientation to the implant orientation data; and outputting, to an associated user, information based on the implant orientation data.

2. The method of claim 1, wherein:

the desired activity is associated with a set of one or more relative orientations between the first bone and the second bone, and the associated original range of motion of the desired activity is achieved when the implant joint formed by the implant pair for the trial orientation allows all relative orientations in the set of one or more relative orientations.

3. The method of claim 1, wherein the determining that the associated original range of motion of the desired activity can be achieved with the implant joint includes determining that the implant joint can reach the associated original range of motion from the zero joint orientation.

4. The method of claim 1, wherein the desired activity has an associated reduced range of motion between the first bone and the second bone, the reduced range of motion being less than the original range of motion, and the determining the implant orientation data includes determining extended implant orientation data based on the desired activity having the associated reduced range of motion.

5. The method of claim 4, further comprising:

tracking, by a medical tracking system operably associated with the computer, an actual orientation of the first implant part relative to the first bone; and determining, by the computer, that the actual orientation is within the range of functional orientations of the first implant part relative to the first bone represented by the extended implant orientation data.

6. The method of claim 1, further comprising tracking, by a medical tracking system operably associated with the computer, an actual orientation of the first implant part relative to the first bone.

7. The method of claim 6, further comprising determining, by the computer, that the actual orientation is within the range of functional orientations of the first implant part relative to the first bone represented by the implant orientation data.

8. The method of claim 1, wherein:

the activity data represents a plurality of desired activities, respective activity implant orientation data is calculated for each of the plurality of desired activities, and the implant orientation data comprises an intersection of the respective activity implant orientation data of all of the plurality of desired activities.

9. The method of claim 1, wherein the implant pair forms a ball-and-socket joint.

10. The method of claim 1, wherein the implant orientation data represents an orientation of the first implant part in two rotational dimensions.

11. A non-transitory computer readable storage medium storing a program for determining implant orientation data representing a range of functional orientations of a first implant part relative to a first bone, the first implant part being part of an implant pair to be implanted in an associated patient, the implant pair comprising the first implant part and a second implant part, the program, which, when running on a computer or loaded onto the computer, causes the computer to:

acquire second implant orientation data representing an orientation of the second implant part relative to a second bone;

acquire implant shape data representing shapes of the first and the second implant parts;

acquire activity data representing a desired activity of the associated patient, the desired activity having an associated original range of motion between the first bone and the second bone;

determine the implant orientation data based on the second implant orientation data, the implant shape data, and the activity data, wherein to determine the implant orientation data the computer is caused to:

determine a zero joint orientation, in which the first and the second bone are in a neutral position relative to each other, of the implant joint based on a trial orientation and the second implant orientation data;

determine, for the trial orientation, that the associated original range of motion of the desired activity can be achieved from the zero joint orientation with an implant joint formed by the implant pair for the trial orientation; and add the trial orientation to the implant orientation data; and output, to an associated user, information based on the implant orientation data.

12. The non-transitory computer readable storage medium of claim 11 wherein:

the desired activity is associated with a set of one or more relative orientations between the first bone and the second bone, and the associated original range of motion of the desired activity is achieved when the implant joint formed by the implant pair for the trial orientation allows all relative orientations in the set of one or more relative orientations.

13. The non-transitory computer readable storage medium of claim 11, wherein the determining that the associated original range of motion of the desired activity can be achieved with the implant joint includes determining that the implant joint can reach the associated original range of motion from the zero joint orientation.

14. The non-transitory computer readable storage medium of claim 11, wherein the desired activity has an associated reduced range of motion between the first bone and the second bone, the reduced range of motion being less than the original range of motion, and the determining the implant orientation data includes determining extended implant orientation data based on the desired activity having the associated reduced range of motion.

15. The non-transitory computer readable storage medium of claim 14, further comprising:

tracking, by a medical tracking system operably associated with the computer, an actual orientation of the first implant part relative to the first bone; and determining, by the computer, that the actual orientation is within the range of functional orientations of the first implant part relative to the first bone represented by the extended implant orientation data.

16. The non-transitory computer readable storage medium of claim 11, further comprising tracking, by a medical tracking system operably associated with the computer, an actual orientation of the first implant part relative to the first bone.

17. The non-transitory computer readable storage medium of claim 16, further comprising determining, by the computer, that the actual orientation is within the range of functional orientations of the first implant part relative to the first bone represented by the implant orientation data.

18. The non-transitory computer readable storage medium of claim 11, wherein:
the activity data represents a plurality of desired activities,
respective activity implant orientation data is calculated for each of the plurality of desired activities, and
the implant orientation data comprises an intersection of the respective activity implant orientation data of all of the plurality of desired activities.

19. The non-transitory computer readable storage medium of claim 11, wherein the implant orientation data represents an orientation of the first implant part in two rotational dimensions.

20. A system for determining implant orientation data representing a range of functional orientations of a first implant part relative to a first bone, the first implant part being part of an implant pair to be implanted in an associated patient, the implant pair comprising the first implant part and a second implant part, the system comprising:

a medical tracking system; and
a computer, the computer being operable to:
acquire second implant orientation data representing an orientation of the second implant part relative to a second bone;
acquire implant shape data representing shapes of the first and the second implant parts;
acquire activity data representing a desired activity of the associated patient, the desired activity having an associated original range of motion between the first bone and the second bone;
determine the implant orientation data based on the second implant orientation data, the implant shape data, and the activity data, wherein to determine the implant orientation data, the computer is further operable to:
determine a zero joint orientation, in which the first and the second bone are in a neutral position relative to each other, of the implant joint based on a trial orientation and the second implant orientation data;
determine, for the trial orientation, that the associated original range of motion of the desired activity can be achieved from the zero joint orientation with an implant joint formed by the implant pair for the trial orientation; and
add the trial orientation to the implant orientation data; and
output, to an associated user, information based on the implant orientation data.

* * * * *